(12) United States Patent
Dasgupta

(10) Patent No.: US 8,728,453 B2
(45) Date of Patent: May 20, 2014

(54) COMBINATORIAL POLYMERIC COMPOSITIONS FOR DRUG DELIVERY

(75) Inventor: Falguni Dasgupta, Bozeman, MT (US)

(73) Assignee: Innovotech, LLC, Bozeman, MT (US)

( * ) Notice: Subject to any disclaimer, the term of this patent is extended or adjusted under 35 U.S.C. 154(b) by 0 days.

(21) Appl. No.: 13/407,388

(22) Filed: Feb. 28, 2012

(65) Prior Publication Data

US 2012/0220749 A1    Aug. 30, 2012

Related U.S. Application Data

(60) Provisional application No. 61/447,532, filed on Feb. 28, 2011.

(51) Int. Cl.
  *A61K 31/74* (2006.01)
(52) U.S. Cl.
  USPC ...................................... 424/78.17
(58) Field of Classification Search
  None
  See application file for complete search history.

(56) References Cited

U.S. PATENT DOCUMENTS

| | | | |
|---|---|---|---|
| 3,706,713 A | 12/1972 | Hull et al. | |
| 3,966,840 A | 6/1976 | Edl et al. | |
| 4,326,049 A | 4/1982 | Rasmussen | |
| 4,686,266 A | 8/1987 | Tang | |
| 5,160,783 A | 11/1992 | Nemoto et al. | |
| 5,221,761 A | 6/1993 | Jen et al. | |
| 5,281,419 A | 1/1994 | Tuan et al. | |
| 5,312,871 A | 5/1994 | Mardare et al. | |
| 5,412,061 A | 5/1995 | King, Jr. et al. | |
| 5,753,726 A | 5/1998 | Reuter et al. | |
| 5,969,060 A | 10/1999 | Arai | |
| 6,355,767 B1 | 3/2002 | Takagi | |
| 6,562,433 B1 | 5/2003 | Ishida et al. | |
| 6,605,691 B1 | 8/2003 | Gross et al. | |
| 7,009,025 B2 | 3/2006 | Kosaka | |
| 7,148,312 B2 | 12/2006 | Kim et al. | |
| 7,235,598 B1 | 6/2007 | Zobel et al. | |
| 7,288,608 B2 | 10/2007 | Bowman et al. | |
| 7,354,978 B2 | 4/2008 | Nishitani | |
| 7,365,148 B2 | 4/2008 | Ono et al. | |
| 7,741,375 B2 | 6/2010 | Benz et al. | |
| 7,772,296 B2 | 8/2010 | Garey, Jr. | |
| 8,133,939 B2 | 3/2012 | Isozaki et al. | |
| 2004/0185029 A1* | 9/2004 | Tang ........................... | 424/78.37 |
| 2006/0173065 A1* | 8/2006 | Bezwada ....................... | 514/419 |
| 2007/0196417 A1* | 8/2007 | Uhrich ........................... | 424/422 |

(Continued)

FOREIGN PATENT DOCUMENTS

| | | |
|---|---|---|
| DE | 3506472 A1 | 8/1986 |
| EP | 0535261 A1 | 4/1993 |
| WO | 2009036229 A1 | 3/2009 |

OTHER PUBLICATIONS

Allcock, Harry R., "Inorganic-Organic Polymers", Adv. Mater, (1994) 6, No. 2, pp. 106-115.

(Continued)

*Primary Examiner* — Paul Dickinson
(74) *Attorney, Agent, or Firm* — LeClairRyan, a Professional Corporation

(57) ABSTRACT

The present invention is directed towards the synthesis of polymeric drug delivery compositions which would address some of the important and difficult to realize aspects of polymer based drug delivery systems by being, biocompatible, stable, capable of achieving desired drug loading, and safe from accidental release while being non-toxic, easy to fabricate and safe for the environment.

19 Claims, 11 Drawing Sheets

General method for radical induced polymerization to produce drug conjugated degradable polymer

(56) References Cited

U.S. PATENT DOCUMENTS

| | | |
|---|---|---|
| 2008/0076821 A1 | 3/2008 | Di Mauro |
| 2008/0095866 A1 | 4/2008 | Declercq et al. |
| 2008/0146766 A1 | 6/2008 | Masubuchi et al. |
| 2009/0029058 A1 | 1/2009 | Grasboeck et al. |
| 2009/0142537 A1 | 6/2009 | Hong et al. |
| 2010/0063209 A1 | 3/2010 | Bowman et al. |
| 2010/0150832 A1 | 6/2010 | Papisov |
| 2010/0210809 A1 | 8/2010 | Simon et al. |
| 2012/0184682 A1 | 7/2012 | Dasgupta |

OTHER PUBLICATIONS

Allcock, H.R., "Macromolecules", Amer. Chemical Society, (Sep. 1983) vol. 16, No. 9, pp. 1401-1406.

Braniste, Viorica et al., "Impact of oral bisphenol a at reference doses on intestinal barrier function intestinal barrier function and sex differences after perinatal exposure in rats", PNAS, (Jan. 2010) vol. 107, No. 1, pp. 448-453.

Duncan, R., "Designing polymer conjugates as lysosomotropic nanomedicines", Biochemical Society Transactions (2007) vol. 35, part 1, pp. 56-60.

Dunn, R.L. and Ottenbrite, R.M., Polymeric Drugs and Drug Delivery Systems, (Eds), ACS Symp. Series, 469 (1991).

Erickson, Britt E., "Bisphenol a Battle", C&EN Washington, www.cen-online.org, (Nov. 2008) pp. 42-45.

Gibson, L., "Baby's Toxic Bottle; Bisphenol a leaching from popular baby bottles", Environmental California Research and Policy Center (2007); ACS Chem. Biol., 3 (2008) 167.

Int'l Searching Authority/US, "Int'l Search Report and Written Opinion", (Nov. 2010) US Patent & Trademark Office, PCT,Int'l Appln. No. PCT/US10/50831.

Chemical & Engineering News, "BPA Craziness", vol. 88, No. 9, pp. 5 (2010).

Chemical & Engineering News, "FDA Raises Flag on Bisphenol A", www.cen-online.org, pp. 8, Jan. 25, 2010.

Chemical & Engineering News (Voith, Melody), "Can Conundrum—Chemists come up short in attempts to remove Bisphenol A from food can liners", www.cen-online.org, pp. 28-29, (2009).

Jain, Rajeev, et al., "Controlled Drug Delivery by Biodegradable Poly(Ester) Devices: Different Preparative Approaches", Drug Development and Industrial Pharmacy, (1998) 24(8), pp. 703-727.

Midori-Horiuti, Terumi et al., "Maternal Bisphenol a Exposure Promotes the Development of Experimental Asthma in Mouse Pups", Environmental Health Perspectives (Feb. 2010), vol. 118, No. 2, pp. 273-277.

Pillai, Omathanu et al., "Polymers in drug delivery", Next Generation Therapeutics, Current Opinion in Chemical Biology 2001, 5: pp. 447-451.

Richards, M., et al., "Evaluation of polyphosphates and polyphosphonates as degradable biomaterials", Jour. of Biomedical Materials Research (1991), vol. 25, pp. 1151-1167.

Shieh, L., et al., "Erosion of a new family of biodegradable polyanhydrides", Jour. of Biomedical Materials Research (1994), vol. 8, pp. 1465-1475.

Sinha,Vivek R., et al., "Bioabsorbable Polymers for Implantable Therapeutic Systems", Drug Development and Industrial Pharmacy, 24(12), pp. 1129-1138 (1998).

* cited by examiner

Figure 1:
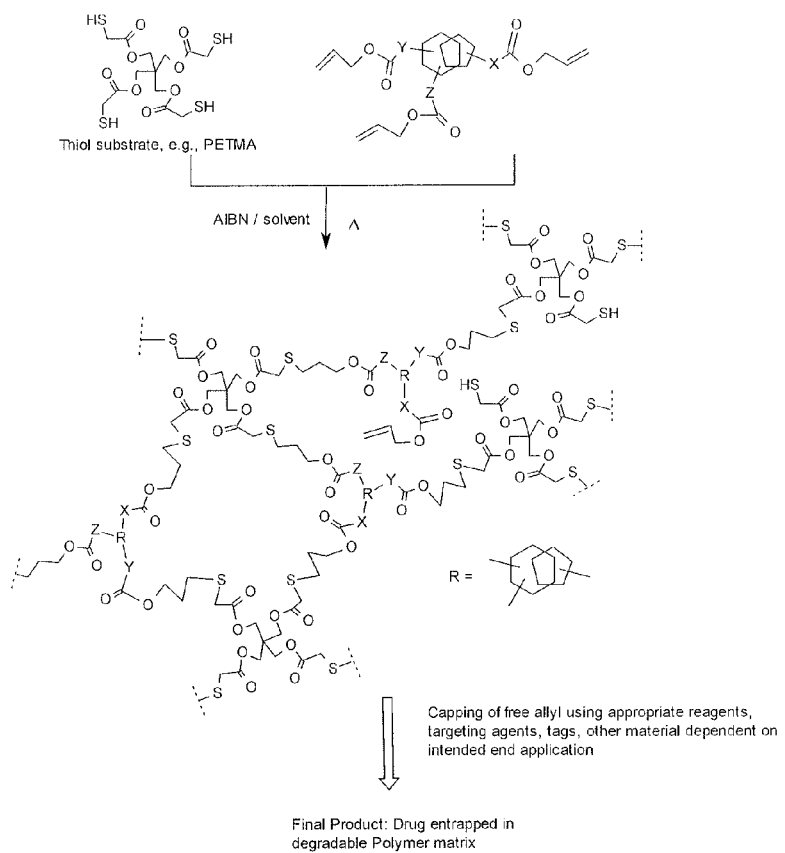

Figure 1. General method for radical induced polymerization to produce drug conjugated degradable polymer Figure 2. Ternary polymerization of a mixture containing PETMA, activated target molecule and activated natural product analog Figure 3. Synthesis of cysteamine conjugated biodegradable polymer composition Figure 4. A ternary biodegradable polymer containing conjugated cysteamine and tetrahydrocurcumin Scheme 4: Synthesis of Prepolymer type 3 and further polymerization Scheme 5: Two step process for the synthesis of drug conjugated biodegradable polymer composition using 'Tetrahydrocurcumin'.

Chart 1: Representative therapeutics for activation and co-polymerization
Note: Arrows indicate the sites where polymerizable functions are introduced via degradable linkers, e.g. carbonates and carbamates Chart 2: Representative Natural products and analogs for activation and co-polymerization
Note: Arrows indicate the sites where polymerizable functions are introduced via degradable linkers, e.g carbonates and carbamates

COMBINATORIAL POLYMERIC COMPOSITIONS FOR DRUG DELIVERY

This application claims the benefit of U.S. Provisional Patent Application No. 61/447,532, filed Feb. 28, 2011, which is incorporated by reference in its entirety for all purposes.

BACKGROUND

For most drugs, and especially for those with cytotoxic side effects, the ideal pharmacokinetic profile will be one wherein the drug concentration reached therapeutic levels without exceeding the maximum tolerable dose and maintains these concentrations for extended periods of time. Encapsulating or conjugating a drug in a biodegradable polymer matrix provides one such way to achieve this desirable end. Polymers could deliver the drug locally and systemically, and do so in a sustained manner, over prolonged period of time. This reduces need for multiple ingestion and better patient compliance. It is also believed that stability of the drug increases since it is not exposed to the physiological conditions in-vivo. Over the last several decades, the technology of polymeric drug delivery has been studied in details (Reviews: K. Al-Tahami and J. Singh, Recent Patents on Drug Delivery & Formulation, 1 (2007) 65-71; V. R. Sinha and L. Khosla, Drug Dev. Ind. Pharm., 24 (1998)1129-1138; R. Langer, Nature, 392(1998) 5-10; W. R. Gombotz and D. K. Pettie, Bioconjug. Chem., 6 (1995) 332-351), and several commercially successful products are now available in the market. Both, non-degradable and degradable polymers can be used for drug delivery purposes. However, the latter type is preferred since the non-degradable variety would require removal of the drug depleted polymer by surgery following treatment. In case of degradable polymers, it is important to ensure that the constituent monomers are not toxic.

Most commonly used biodegradable polymers are Polylactide (PLA) and Poly(Lactide-co-Glycolide) (PLGA) [George Boswell and Richard Scribner, U.S. Pat. No. 3,773,919 (1970); R. S. Tuan, S. S. Lin, U.S. Pat. No. 5,281,419 (1994)]. Although using PLA and PLGA based polymers is advantageous due to their historic use and acceptance, commercialization of newer products based on these polymers may be difficult since more than 500 patents have been issued for various applications of these polymers. PLA and PLGA polymers also have inherent limitations in terms of flexibility for applications. Due to this, several polyesters, polyamides, and polyesteramides (PHB, PBS, PEA, TPA, PHBV, PBSA, PBAT) have found their way as second generation biodegradable polymers. Some of these and other new players are continuing to be tested and under development, e.g., natural and synthetic Polyketals [M. I. Papisov, US Patent Application 20100150832 (2010); Murthy at al., Biomaterials, 31 (2010) 810-817; Benz et al., U.S. Pat. No. 7,741,375 (2010)], Polyorthoesters [Heller et al., Eur. J. Pharm. Biopharm., 50 (2000)121-128], Polyphosphazines [H. R. Allcock, et al., Macromolecules, 16 (1983) 1401; H. R. Allcock, Advanced Materials, 6 (1994)106], Polyanhydrides [L. Shieh, et al., J. Biomed. Mater. Res., 28 (1994) 1465-1475], Polyphosphoesters [M. Richards, et al., J. Biomed. Mater. Res., 25 (1991) 1151], Polyesters [R. Jain, et al., Drug Dev. Ind. Pharm., 24 (1998) 703-727]. Hydrogels that can respond to a variety of physical, chemical and biological stimuli have been used to design of closed-loop drug-delivery systems [O. Pillai and R. Panchagnula, Curr. Opin. Chem. Biol., 5 (2001) 447-451]. Antimicrobial Polyurethane Resins have been prepared by incorporating antimicrobial during the synthesis of a resin and the product was suitable for molding into medical devices (U.S. Pat. No. 7,772,296, filed 2007).

Novel supramolecules made from polyethylene oxide copolymers and dendrimers have been examined for delivery of genes and macromolecules ['Polymer in drug delivery', O. Pillai and R. Panchagnula, Curr. Opin. Chem. Biol., 5 (2001) 447-451]. Biodegradable Polymer that released fluoroquinolone antibiotic has been developed by conjugating the antibiotic to poly(ε-caprolactone) diol using diisopropylcarbodiimide [S. Y. Han, S. H. Yoon, K. H. Cho, H. J. Cho, J. H. An, and Y. S. Ra, J. Korean Med. Sci., 20 (2005) 297-301]. Polymer barrier layer has been successfully used to effect controlled release of high blood pressure drug Sular (nisoldipine) from its core made from hydroxypropyl methycellulose (HPMC) and the active ingredient (Sciele and SkyePharma). 'Smart polymers' have been used to deliver peptide and protein drugs. These can be classified as, temperature sensitive polymers, namely, poly(N-isopropylacryl-amide) (PNIPAAM), poly(ethylene oxide)-poly(propylene oxide)-poly(ethylene oxide) triblock copolymers (PEO-PPO-PEO), poly(ethylene glycol)-poly(lactic acid)-poly(ethylene glycol) triblocks (PEG-PLAPEG); phase sensitive polymers, such as, poly(D,L-lactide), poly(D,L-lactide-co-glycolide) and poly(D,L-lactide-co-ε-caprolactone); pH sensitive polymers, such as, anionic pH-sensitive polymers like polyacrylic acid (PAA) (Carbopol®) or its derivatives, polymethacrylic acid (PMAA), poly(ethylene imine), poly(L-lysine), poly(N, N-dimethyl aminoethyl methacryl amide), poly(methacrylic acid-γ-ethylene glycol) P(MAA-g-EG). In the case of most 'smart polymers' the peptide/protein drug is physically entrapped within the polymer matrix and slowly released as the polymer degraded. Polymer conjugated anticancer drugs have been studied using polymers such as HPMA [N-(2-hydroxypropyl)methacrylamide] copolymers, PGA [poly (glutamic acid)], PEG [poly(ethylene glycol)] and polysaccharides (e.g. dextran). Details of HPMA copolymer anticancer conjugates and their clinical study has been reviewed [R. Duncan, Biochemical society Transactions, 35, part 1 (2007) 56-60].

In summary, biodegradable polymers for drug delivery purposes are hydrophilic, hydrophobic or a mixture of both, and can also include hydrogels. The therapeutic agent is either physically entrapped during or following the polymerization process or (a) attached covalently to the monomer prior to polymerization and (b) conjugated to a prefabricated polymer via reactive functionalities present on the polymer, on therapeutic agent or both. [Reviews: 'Drug Delivery Systems, Section 7.14, by J. Heller and A. S. Hoffman, in Biomaterial Science: An introduction to material in medicine, B. D. Ratner (Ed.), 2004//books.googles.com/books; E. W. Neuse, Metal-based Drugs, vol. 2008 (2008), Article ID 469531; A. K. Bajpai, S. K. Shukla, S. Bhanu and S. Kankane, Prog. Polymer Sci., 33 (2008) 1088-1118; R. L. Dunn and R. M. Ottenbrite (Eds), ACS Symp. Series, 469 (1991)].

More recently, 'click' chemistry has been used to make polymers from suitably derivatized monomers. The 'click' approach for making complex molecules has been described [H. C. Kolb, et al., Angew. Chem., Int. Ed., 40 (2001) 2004-2021] and its applications in making polymeric material has been recently reviewed [A. B. Lowe, Polym. Chem., 1 (2010) 17-36]. Thiol-ene photopolymerization has been used to fabricate PEG-based hydrogels [Biomacromolecules, 9 (2008) 1084-1087], and the technique utilized to make protein entrapped, crosslinked, hydrogel preparation for therapeutic end use [A. A. Aimetti, et al., Biomaterials, 30 (2009) 6048-6054].

BRIEF DESCRIPTION

We hereby describe a versatile, combinatorial approach for the preparation of polymeric drug delivery compositions, with the option to use sustainable "green chemicals" and their suitable derivatives. In certain embodiments of this invention, for every 'active molecule' to be delivered, (e.g., a therapeutic, nutraceutical, an imaging agent, or other such active chemical entities and biologics), it will be possible to choose one or more monomers/prepolymers from a selected pool that have been prepared from biocompatible, sustainable, non-toxic chemicals, preferably obtained from non-petroleum sources. In yet another embodiment of the invention, these monomers and prepolymers made therefrom, while intrinsically suitable for polymerization under appropriate conditions, may also be derivatized to afford biodegradable polymers. By choosing starting compounds from a pool of monomers and prepolymers obtained directly or modifying natural products, as well as carefully chosen, commercially available, non-toxic intermediates, it will be possible to make a library of polymer compositions in combination with each target candidate, whose content in the final composition can be varied as desired. Ideally, this will provide a family of polymer compositions for each active compound, where each new composition can have different degradation profile. The final polymeric product will not only be degradable and deliver the active molecule, but the degradation products from the polymer will be non-toxic and may even support health by being FDA approved GRAS designated nutraceuticals.

The monomers or prepolymers used in this invention can be any suitable monomer or prepolymer that is known in the art. The term "prepolymer" refers to a monomer or system of monomers that have been reacted to an intermediate molecular weight state. This material is capable of further polymerization via its reactive end groups. As such, mixtures of reactive polymers with un-reacted monomers may also be referred to as prepolymers. The term "prepolymer" and "polymer precursor" may be interchanged.

The "active molecule" to be delivered can be any suitable drug, active agent, nutraceutical, imagining agent or the like known in the art.

The nature of the functional groups selected for the monomers as well as prepolymers and those present on the active ingredients, complement each other in terms of reactivity. So that, given appropriate stimuli, they can react to form polymeric, biodegradable compositions.

In one embodiment of the invention, the functionalities on all the reactive substrates were chosen from among those that are amenable to 'click' chemistry. Thus, each monomer, prepolymer, active molecule, and linker moieties may constitutively possess various chemical groups, e.g., among others, esters, ethers, amides, carbamates, carbonates, thiocarbonates, thiocarbamates, and guanidine, the reactive end groups displayed on them for the purpose of polymerization can be chosen from, allyl, propargyl, vinyl, azido and thiol.

In certain embodiments of this invention the monomers and prepolymeric intermediates, comprise functional groups which complement the reactive functions on the 'active molecule' in such away that the final polymerization can be conducted with minimum chemical burden, e.g., by photoinduced or chemically induced free radical polymerization.

This approach allows the predetermined loading of an 'active molecule' by adjusting its quantity or that of its suitably 'armed derivative' in the mixture of monomers and prepolymers before subjecting the mixture to polymerization. It is expected that all the active component will be incorporated within the polymer via biodegradable linker. This is in contrast to the currently available methodologies, wherein the 'active ingredients' are either entrapped physically within the matrices during polymerization or chemically attached on to the polymer following polymerization, following which a quantitative analysis would determine the exact loading of the 'active ingredient'. The new polymer compositions of this invention may be described as 'active molecule conjugated hydrid material', since the active components in this invention are themselves in the form of a monomer or a prepolymer. Additionally, with appropriate choice of monomers and prepolymers, the final polymer composition, containing the 'active molecule', may be further ornamented with a targeting agent.

As an example, drug incorporated degradable polymers were prepared using Cysteamine as the releasable 'active molecule'.

Cysteamine has been designated as on orphan drug, and as its bitartrate salt in tablet form called 'Cystagon', it is used to treat 'Cystinosis'. [Cystinosis is caused by a defect in transport of cystine across the lysosomal membrane due to defective function of the lysosomal membrane protein cystinosin, resulting from mutations of the cystinosis gene (CNTS). For details and references check http://ghr.nlm.nih.gov/condition/cystinosis]. Cystagon must be consumed several times a day for it to be effective and causes many adverse side effects. Studies conducted to understand the pharmacokinetics of cysteamine suggest slow release formulation is more effective and should result in improved patient compliance [R. Dohil et al., J. Pediatrics, 156 (2010) 71-75].

Figure 3:
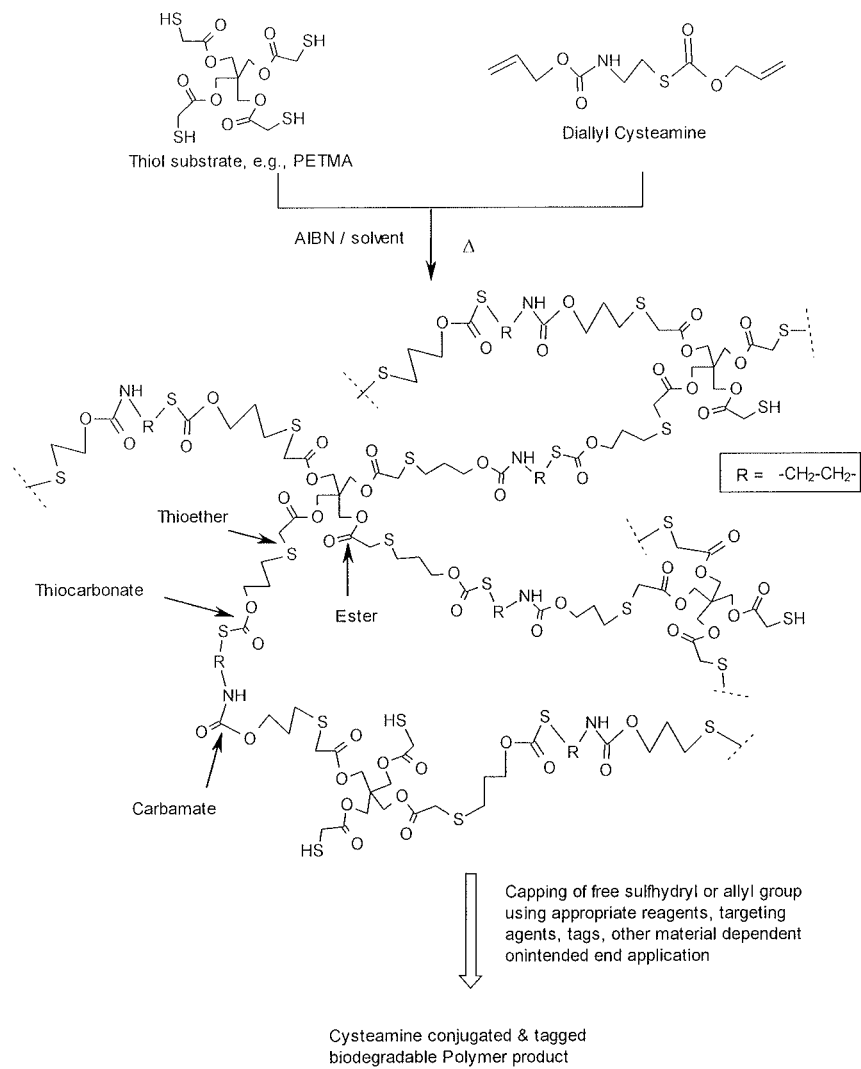
Figure 4:
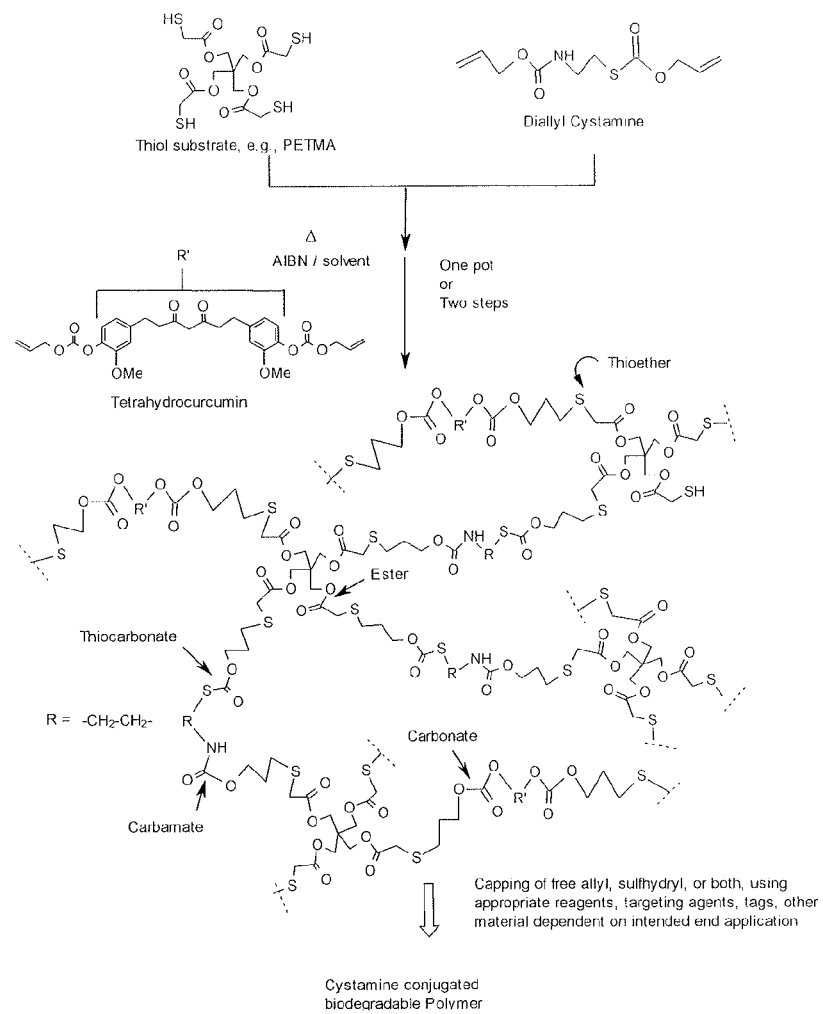

Allyloxycarbonyl derivative of cysteamine was prepared and copolymerized with pentaerythritol tetrakis 2-mercaptoacetate (PETMA), in the presence of a radical initiator, 2'-azobisisobutyronitrile (AIBN), to afford a degradable polymer containing ester, carbamate and thiocarbonate as hydrolysable linkers (FIG. 3). In a second preparation, di-allyloxycarbonyl derivative of tetrahydrocurcumin was incorporated in addition to the above mentioned mix of two components to give a three component copolymer where PETMA effectively forms a bridge between cysteamine and tetrahydrocurcumin, a natural product analog (FIG. 4).

One objective of the invention is to be able to make biodegradable polymer matrices using more than one component, wherein at least one component is a therapeutic substance.

Another objective is to make biodegradable polymer matrices using a ternary system wherein at least one of the components is a natural product.

Yet another objective is to make the above two types of biodegradable polymers in a way such that in-vitro or in-vivo degradation of these polymers will generate the original drug substance and/or the natural product, depending on the nature of the polymer composition.

Fourth objective is to activate the drug substance or the natural product by introducing a functional group that can be involved in polymerization.

Yet another objective is to introduce the above 'polymerizable functional groups' in a way such that they are attached to the drug substance or the natural product via one or more degradable linkers in order to fulfill the third objective.

One other desirable objective is to make ternary polymers in which at least two of the components are: 1) a drug substance and 2) a natural product (preferably chosen from those well known as antioxidant, anti-inflammatory, and such other), both of which are activated for the purpose of polymerization.

A seventh objective is to make biodegradable oligomers/prepolymers of the drug substance, and the natural product and use them for making block polymers and block co-polymers.

The eighth objective is to prepare combinatorial polymers of desired compositions using various combinations of active monomers and prepolymers made from a drug substance and a natural product.

Another desirable objective is to utilize 'click chemistry' for the final polymerization step.

One major objective is to use such polymer compositions to deliver active molecules by, oral, transmucosal, transdermal, topical, nasal, parental, intravenous, intraperitoneal or any other effective route of administration.

FIGURES

FIG. 1: General approach for the preparation of 'active molecule' incorporated biodegradable polymer.

Figure 2:
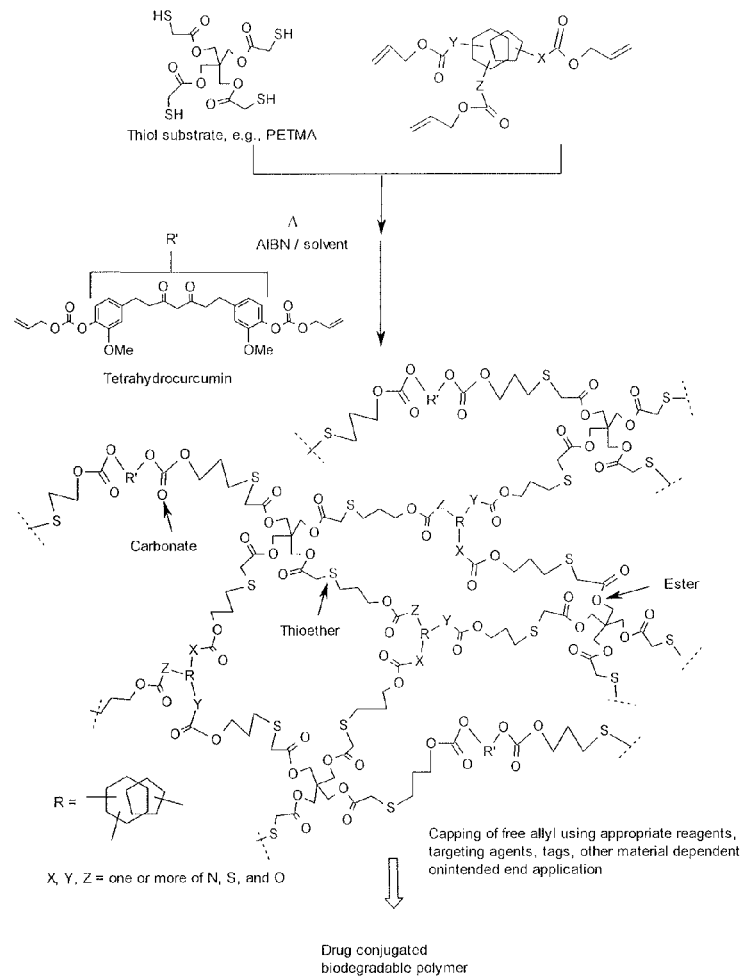

FIG. 2: Two step process for making drug conjugated ternary polymers.

FIG. 3: Synthesis of cysteamine conjugated biodegradable polymer composition.

FIG. 4: Biodegradable polymer using a ternary composition of cysteamine, tetrahydrocurcumin and PETMA.

Figure 5:
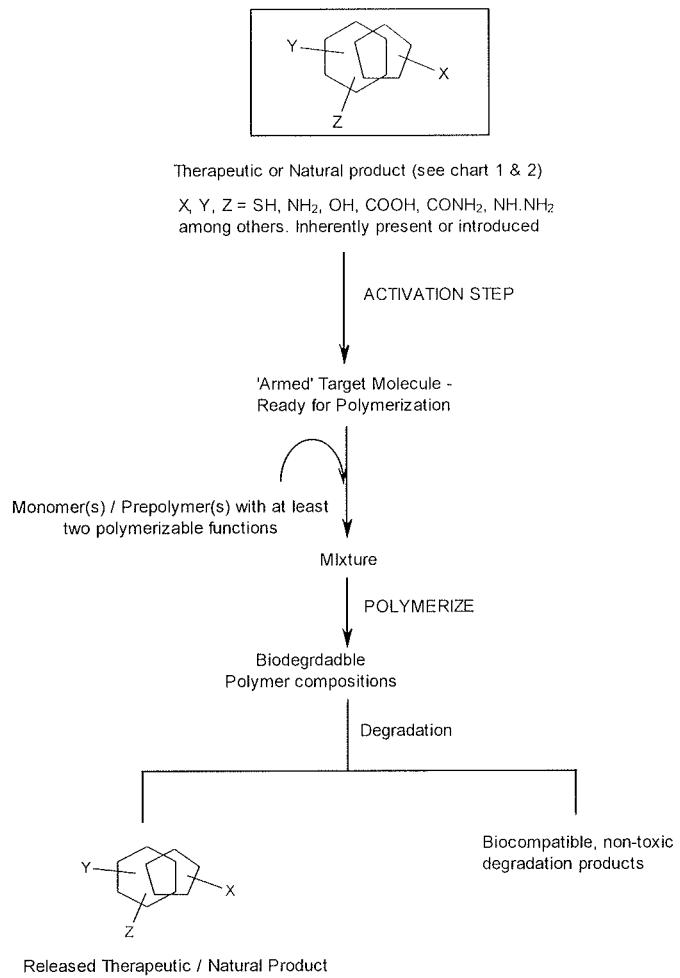

FIG. 5: Scheme 1. General concept for making 'active molecule' embedded biodegradable polymer.

Figure 6:
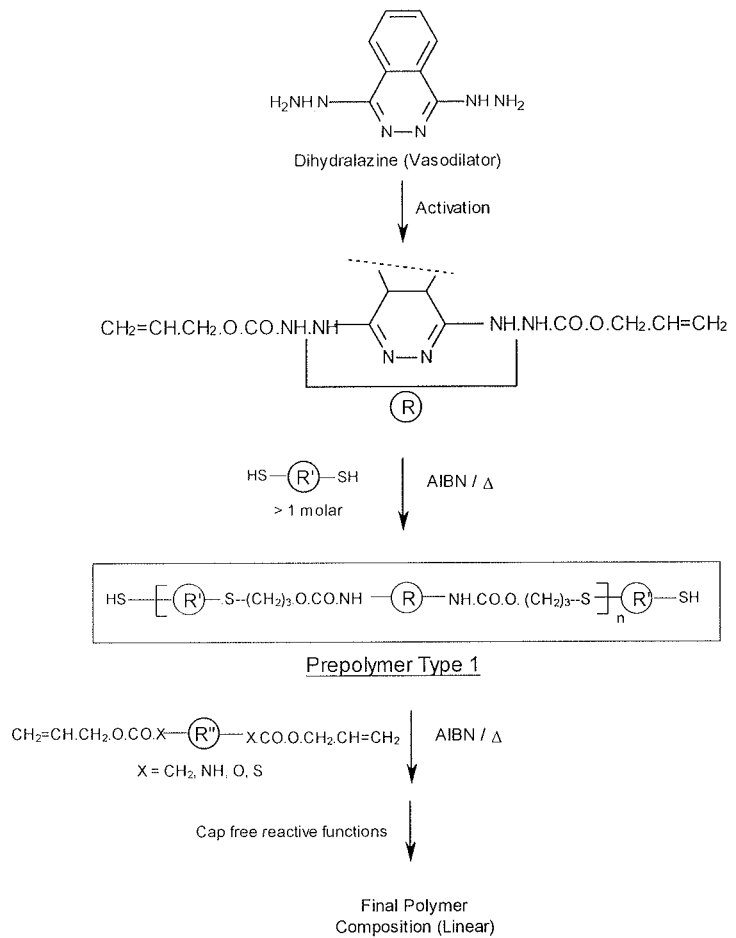

FIG. 6: Scheme 2. Synthetic route to prepolymer type 1 (dithiol) and its subsequent polymerization.

Figure 7:
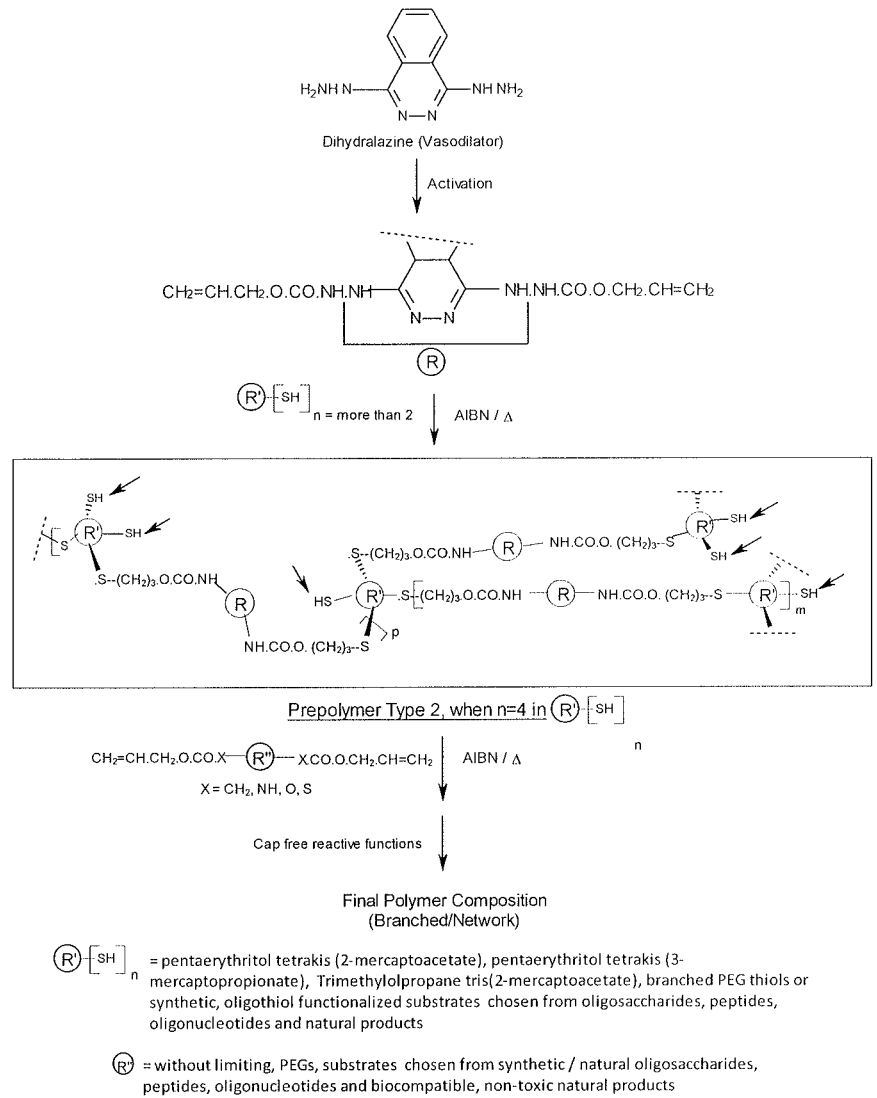

FIG. 7: Scheme 3. Synthetic route to prepolymer type 2 (multithiol) and its subsequent polymerization.

Figure 8:
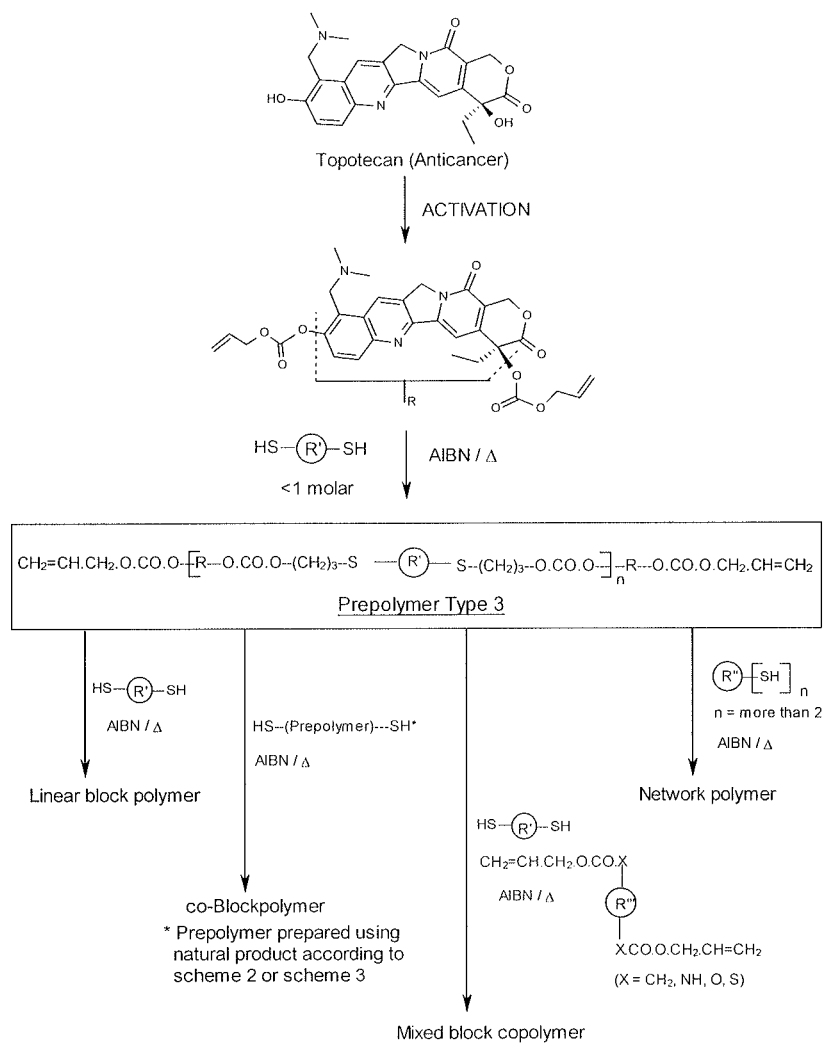

FIG. 8: Scheme 4. Synthetic route to prepolymer type 3 (diallylcarbonate) and its subsequent polymerization.

Figure 9:
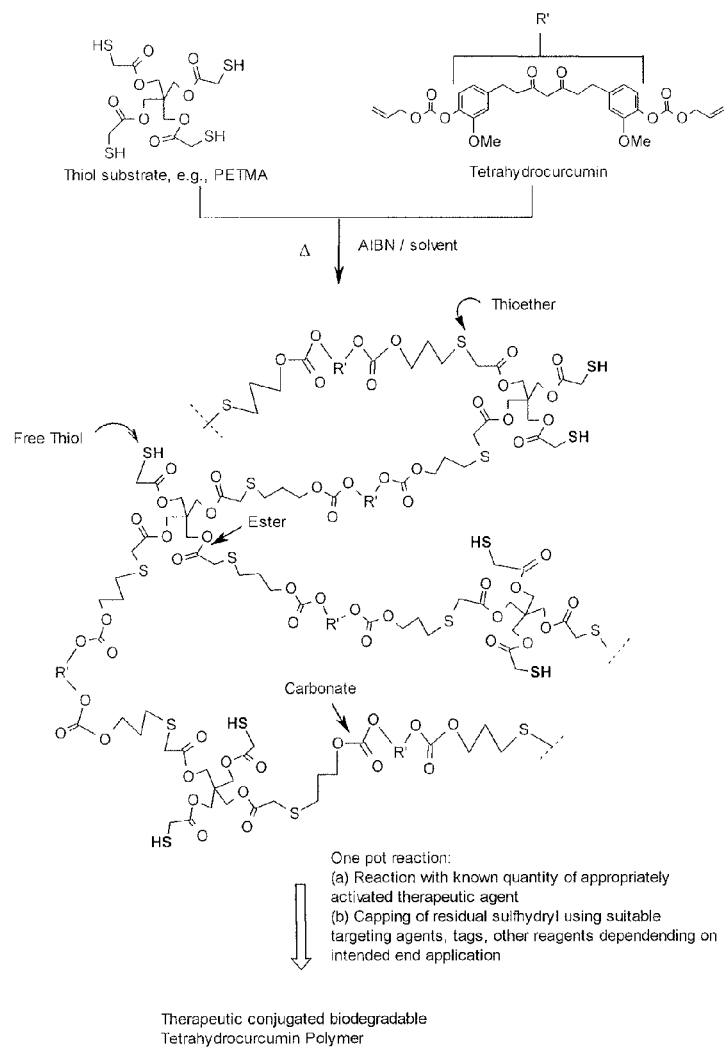

FIG. 9: Scheme 5. Two step process for the synthesis of drug conjugated biodegradable polymer composition.

Figure 10:
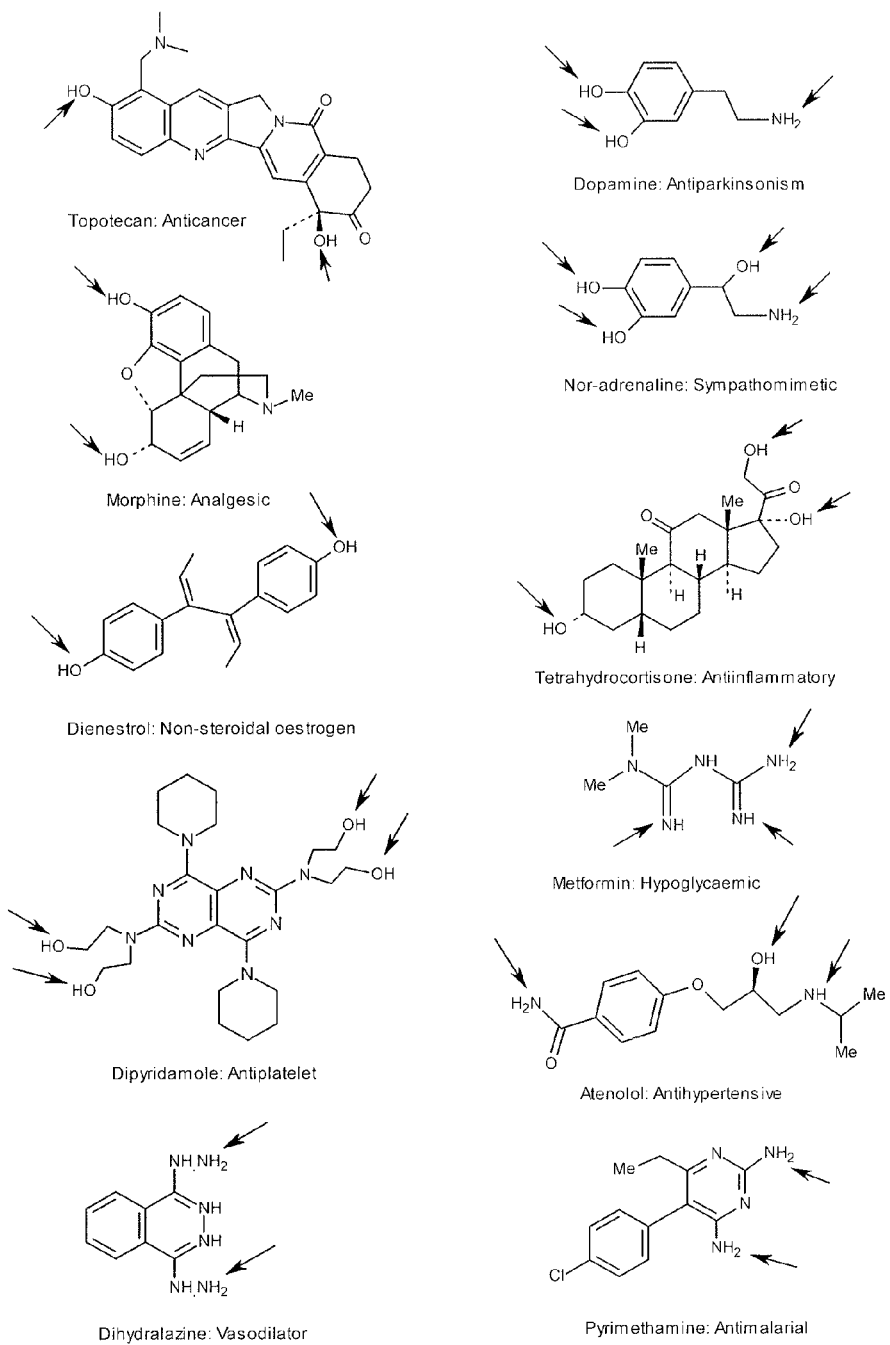

FIG. 10: Chart 1. Representative therapeutics for activation and copolymerization.

Figure 11:
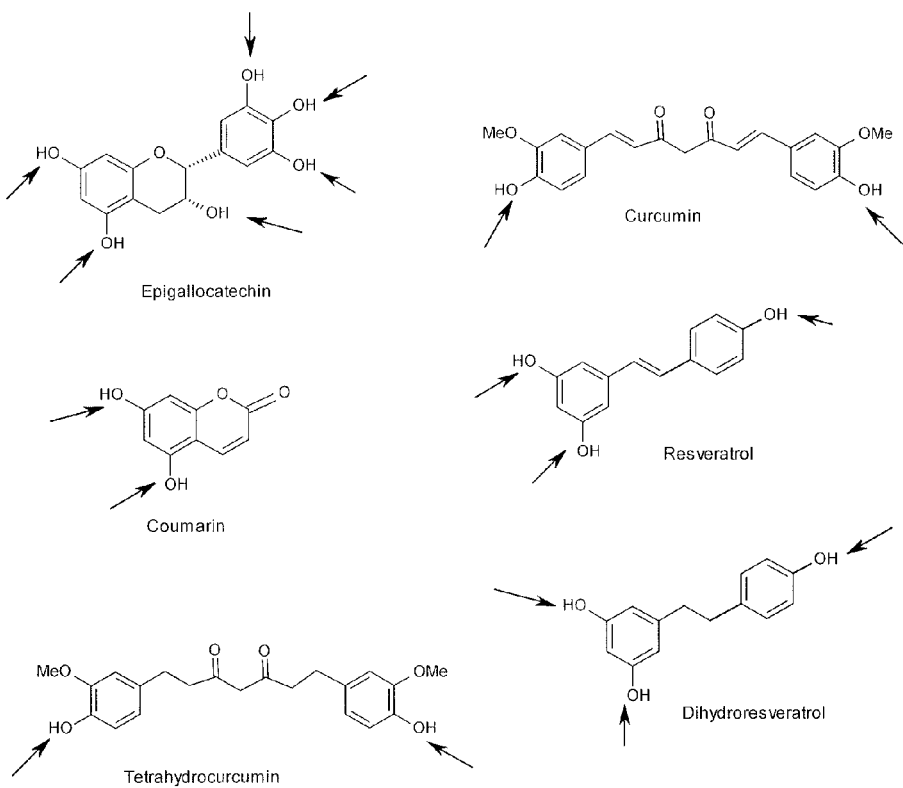

FIG. 11: Chart 2. Representative natural products for activation and copolymerization

DETAILED DESCRIPTION

General Process for Making 'Active Agent' Incorporated Biodegradable Polymers

Suitably functionalize the target molecule, i.e., therapeutic, nutraceutical or other bioactive molecules ('active molecule') that will be incorporated into the polymer. This would involve arming the target molecule (FIG. 10, 11) with a polymerizable function (such as allyl, vinyl, thiol, propargyl) that is attached via a degradable linker (FIG. 1, 5).

Mix the 'active molecule', and suitable monomer or polymer precursors in predetermined stoichiometry and polymerize, e.g., a target pharmaceutical, armed with cleavable allyl or propargyl functions, can be polymerized in the presence of a monomer or a prepolymer having two or more thiol functions, by irradiation or by heating in the presence of a free radical initiator (FIG. 1-4, 6-9).

Optionally, a ternary system containing an appropriately armed therapeutic, an armed natural product and a third commercially available monomer of choice can be copolymerized to provide a novel biodegradable polymer composition (FIG. 2, 4). It is noteworthy that the ratios of each monomer as well as the nature of the degradable bonds can be varied providing an opportunity to create a combinatorial family of polymer compositions. Also, the ternary reaction can be carried out in one or more than one step. In one case, all three components can be mixed together and polymerized whereas in another case, first two components may be polymerized to form a prepolymer (optionally, a copolymer or a block co-polymer) which is further reacted with the third component. Example of a two step process is demonstrated in FIG. 9, where a drug component in its activated form can be incorporated into a two component polymer (optionally, a prepolymer, a copolymer or a block co-polymer), in predetermined quantities.

This combinatorial approach provides a powerful method for quickly preparing a number of biodegradable polymer compositions while controlling the loading of a drug substance as well as the amount of desirable natural products within the polymer matrices.

The ability to incorporate more than one component, especially the use of non-toxic, nutraceutically relevant natural products, more specifically natural antioxidants, has not been done before, and expands the scope as well as acceptance of biodegradable polymer based drug delivery formulations. This process also allows a judicious combination of hydrophilic and hydrophobic components in the final composition. Thus, it is possible to prepare hybrid polymers either with random distribution of such regions or build polymers having blocks that are hydrophilic, hydrophobic or both.

Synthesis of cysteamine incorporated degradable polymers (FIG. 3, 4) exemplifies the feasibility of this approach and opens up opportunities to prepare similar drug incorporated polymeric compositions using other well known drugs (FIG. 10) as well as other therapeutics that are currently under development.

EXAMPLES

General Method for Preparation of Allyl Carbonate, Carbamate and Thiocarbonate

Weighed quantity of substrate is dissolved in a previously dried, suitable aprotic solvent, e.g., Chloroform, Dichloromethane, N,N-Dimethylformamide (N,N-DMF), p-Dioxane, Tetrahydrofuran (THF), among others, in the presence of more than equimolar (w.r.t. reactive functions) proportions of Pyridine (usually more than 3 molar excess), maintained between $-20°$ C. to r.t. (20-25° C.), preferably 0-5° C., and requisite quantity of allyl chloroformate (at least 1.1 molar /reactive group) is added into the stirred solution of the substrate while maintaining the temperature. Reaction is monitored by tlc until completion, i.e., when no starting material is visible. In some cases the temperature is allowed to rise to r.t. for the reaction to come to completion. Adequate quantity of methanol (ACS grade) is added and stirred (1-2 h) to destroy any excess reagent.

On completion, the reaction mixture is diluted with chloroform, the organic solution is washed successively with water, cold aqueous HCl (1N), water, cold aqueous sodium bicarbonate, and finally with water and dried (anhyd. $MgSO_4$). Filtration and evaporation of the organic solution gives the allyl functionalized derivative. A quick column chromatography gives the pure product.

N,S-Di-(Allyloxycarbonyl)-Cysteamine (Cysteamine Diallylcarbonate, FIG. 3, 4)

Cysteamine hydrochloride (1 g, 8.8 mM) was dissolved in dichloromethane (DCM, 6 mL) containing pyridine (3 mL) and the solution cooled ($-10°$ C.). A solution of allyl chloroformate (2 mL, 18.86 mM) in DCM (3 mL) was dropwise added into the stirred cold cysteamine solution. Following the addition, reaction temperature was allowed to rise to room temperature (22° C.), when tlc (Hexane-Ethyl acetate, 2:1;

6:1 v/v) indicated product. Methanol (2 mL) was added followed by CHCl$_3$ (10 mL), stirring continued for 2 h following which the reaction mixture was transferred into a separating funnel and washed (general method). Organic layer was dried (MgSO$_4$), filtered, evaporated under vacuum to a syrup and column chromatographed (prepacked silica, 40 g) using hexane-ethyl acetate (12:1 v/v) to give the name compound (1.6 g).

$^1$H-NMR, (ppm, CDCl$_3$). 5.9 (m, —CH= of allyl, 2 proton), 5.2 (m, —CH=CH$_2$ of allyl, 4 proton), 4.7-4.4 (2d, —CH$_2$—CH=CH$_2$ of allyl, 4 proton), 3.4 and 2.9 (two t, 2 proton each, N—CH$_2$—CH$_2$—S).

Radical Initiated Polymers: Cysteamine Conjugated Polymers.

Type I (FIG. 3): Reaction Between Cysteamine Diallyl Carbonate and PETMA.

PETMA (1 g, 2.3 mM) was transferred into r.b.flask (25 mL), fitted with a condenser and dissolved in dry p-Dioxane (5 mL). The solution was warmed (75° C., oil bath) and kept stirred magnetically. The assembly was purged with nitrogen and azo bis-isobutyronitrile (AIBN, 15 mg) was added, followed by a solution of cysteamine diallyl carbonate (1.15 g, 4.69 mM) in p-dioxane (3.5 mL). Temperature of the bath was raised to 98° C. Within 2 h, a gel like solid formed. The Bath temperature was reduced down to 75° C. and reaction was allowed to continue (8 h). The solid was broken up, transferred into ethanol (20 mL), thoroughly triturated and the supernatant discarded. The soft solid was triturated and washed (×2) with ethanol before filtering and drying under vacuum. Yield: 2.1 g.

Type II (FIG. 4): Reaction Between Cysteamine Diallyl Carbonate, Tetrahydrocurcumin Diallyl Carbonate and PETMA.

Reaction was similarly carried out using PETMA (0.44 g, 1.01 mM in p-dioxane, 5 mL), AIBN (15 mg), cysteamine diallyl carbonate (0.25 g, 1.02 mM, in p-dioxane 3 mL) and tetrahydrocurcumin diallylcarbonate (0.55 g, 1.01 mM in p-dioxane 1.7 mL). First, the solution of cysteamine diallyl carbonate was added into the PETMA solution containing AIBN, and reacted for 2 h (98° C.). This was followed by transferring the solution of tetrahydrocurcumin diallyl carbonate into the reaction mixture and reaction continued at 98° C. Shortly (30 min) a gel like solid formed. Reaction was continued at 98° C. (2 h), bath temperature reduced to 75° C. and after 8 h, worked up as in the previous experiment. Yield: 1.2 g.

The foregoing detailed description has been given for clearness of understanding only and no unnecessary limitations should be understood there from as modifications will be obvious to those skilled in the art.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

The disclosures, including the claims, figures and/or drawings, of each and every patent, patent application, and publication cited herein are hereby incorporated herein by reference in their entireties.

What is claimed is:

1. A method of making a combinatorial library of biodegradable polymeric compositions, comprising the steps of:

a. arming/derivatizing an active molecule and optionally a natural product with at least one hydrolysable linker having at least one reactive end group to form an armed/derivatized active molecule and optionally an armed/derivatized natural product;
   b. mixing predetermined stoichiometry of one or more monomers having at least two polymerizable functionalities with the armed/derivatized active molecule and optionally the armed/derivatized natural product to form mixtures;
   c. co-polymerizing the armed/derivatized active molecule and optionally the armed/derivatized natural product of the mixtures obtained in step (b) to form pools of pre-polymers;
   d. mixing and copolymerizing predetermined stoichiometry of the pre-polymers obtained in step (c) with selected monomers to obtain said polymeric compositions;
   e. treating said polymeric compositions with capping reagents to give a combinatorial library of biodegradable polymeric compositions, wherein the biodegradable polymeric compositions allow a predetermined loading of the active molecule or the armed active molecule by adjusting quantity of said active molecule or said armed active molecule in said mixture before subjecting the mixture to polymerization, and
   further wherein the active molecule is selected from the group consisting of drugs, nutraceuticals, and imaging agents, and the natural product is a naturally occurring plant polyphenol or derivative thereof; and wherein said reactive end groups and functionalities are selected from the group comprising thiol, allyl, amine, anhydride, azido, carboxy, epoxy, hydroxy, isocyanate, lactone, propargyl, thiocyanate, or vinyl.

2. The method of claim 1, wherein the active molecule is functionalized with two or more hydrolysable linkers having at least two reactive end groups.

3. The method of claim 1, wherein the polymer is formed in one step or more than one steps.

4. The method of claim 2, wherein the end groups are selected from the group consisting of allyl, vinyl, azido, propargyl and thiol.

5. The method of claim 1, wherein the one or more monomers is selected from the group consisting of commercial materials selected from pentaerythritol tetrakis (2-mercaptoacetate), pentaerythritol tetrakis (3-mercaptopropionate), Trimethylolpropane tris(2-mercaptoacetate), Dimercaptosuccinic acid, 2,3-Dimercaptopropanol, 1,4-Dithiothreitol, 1,4-Butanedithiol, 2-mercaptoethyl ether and thiol-PEGs, or synthetic, oligothiol functionalized substrates selected from oligosaccharides, peptides, oligonucleotides and natural products.

6. The method of claim 1, wherein the prepolymer comprises at least two reactive thiol end groups.

7. The method of claim 1, wherein the prepolymer comprises at least two reactive end groups other than thiol, wherein said at least two reactive end groups are selected from the group consisting of allyl, vinyl, azido or propargyl.

8. The method of claim 1, wherein the natural product is a naturally occurring plant polyphenol, analog or derivative thereof.

9. The method of claim 8, wherein the plant polyphenol, analog or derivative thereof is selected from the group consisting of curcumin, tetrahydrocurcumin, resveratrol, dihydroresveratrol, curcumin diallyl carbonate, tetrahydrocurcumin diallyl carbonate, resveratrol triallyl carbonate, mono- O-allyl curcumin, tetra-allyl curcumin, di-allyl tetrahydrocurcumin, tetra-allyl tetrahydrocurcumin, di-O-allyl resveratrol and tri-O-allyl resveratrol.

10. A biodegradable polymeric composition, synthesized by the method of claim 1, comprising at least one monomer selected from allyl, propargyl or vinyl functionalized active molecule.

11. The biodegradable polymeric composition of claim 1, wherein the monomer is selected from the group consisting of pentaerythritol tetrakis (2-mercaptoacetate), pentaerythritol tetrakis (3-mercaptopropionate), Trimethylolpropane tris(2-mercaptoacetate), Dimercaptosuccinic acid, 2,3-Dimercaptopropanol, 1,4-Dithiothreitol, 1,4-Butanedithiol, 2-mercaptoethyl ether and thiol-PEGs.

12. A biodegradable polymeric composition, synthesized by the method of claim 1.

13. The biodegradable polymeric composition of claim 12, wherein said polymer is a linear co-polymer, block co-polymer, mixed block copolymer, crosslinked polymer or network polymer.

14. The biodegradable polymeric composition of claim 12, wherein the natural product is a naturally occurring plant polyphenol or derivative thereof.

15. The biodegradable polymeric composition of claim 12, wherein the plant polyphenol or derivative thereof is selected from the group consisting of curcumin, tetrahydrocurcumin, resveratrol, or dihydroresveratrol, curcumin diallyl carbonate, tetrahydrocurcumin diallyl carbonate, resveratrol triallyl carbonate, mono-O-allyl curcumin, tetra-allyl curcumin, di-allyl tetrahydrocurcumin, tetra-allyl tetrahydrocurcumin, di-O-allyl resveratrol and tri-O-allyl resveratrol.

16. The biodegradable polymeric composition of claim 12, wherein the active molecule is

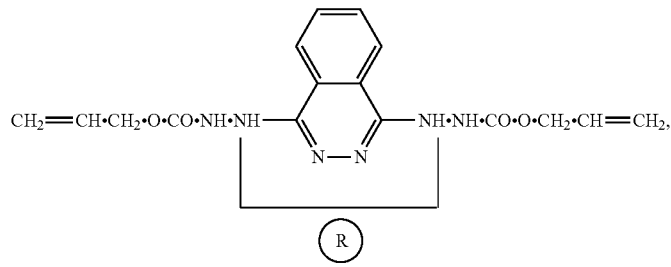

the monomer is

the prepolymer is

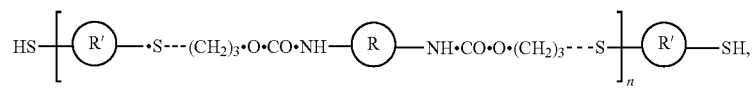

a second monomer is

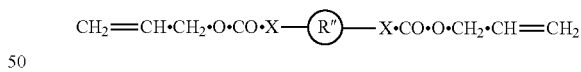

and the polymer is

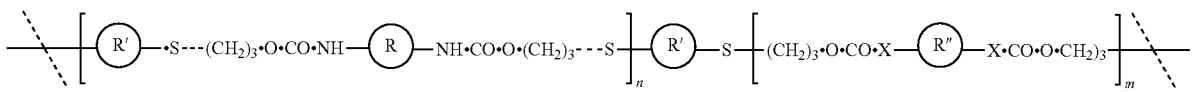

wherein,

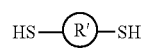

is selected from a group comprising dimercaptosuccinic acid, 2,3-dimercaptopropanol, 1,4-dithiothreitol, 1,4-butanedithiol, 2,3-dimercapto butane, 2-mercaptoehtyl ether, dithiol-PEG or dithiol containing substrates selected from oligosaccharides, peptides, oligonucleotides, and natural products;

"X" is selected from a group comprising $CH_2$, NH, O or S; and

is selected from a group comprising PEGs, substrates selected from synthetic and natural oligosaccharides, peptides, oligonucleotides, and biocompatible natural products.

17. The biodegradable polymeric composition of claim 12, wherein the active molecule is

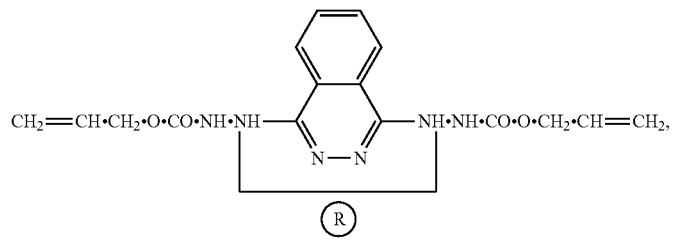

the monomer is

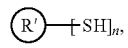

the prepolymer is

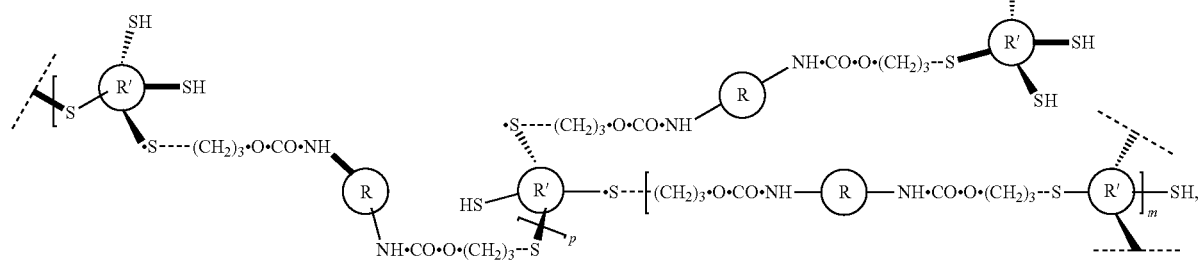

a second monomer is

and the polymer is a cross linked polymer, wherein

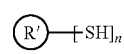

is selected from a group comprising pentaerythritol tetrakis (2-mercaptoacetate), pentaerythritol tetrakis (3-mercaptopropionate), Trimethylolpropane tris(2-mercaptoacetate), branched PEG thiol or synthetic oligothiol functionalized substrates selected from oligosaccharides, peptides, oligonucleotides, and natural products, "X" is selected from a group comprising $CH_2$, NH, O or S; and

is selected from a group comprising PEGs, substrates selected from synthetic and natural oligosaccharides, peptides, oligonucleotides, and biocompatible natural products.

18. The biodegradable polymeric composition, synthesised by the method of claim 12, wherein the active molecule is

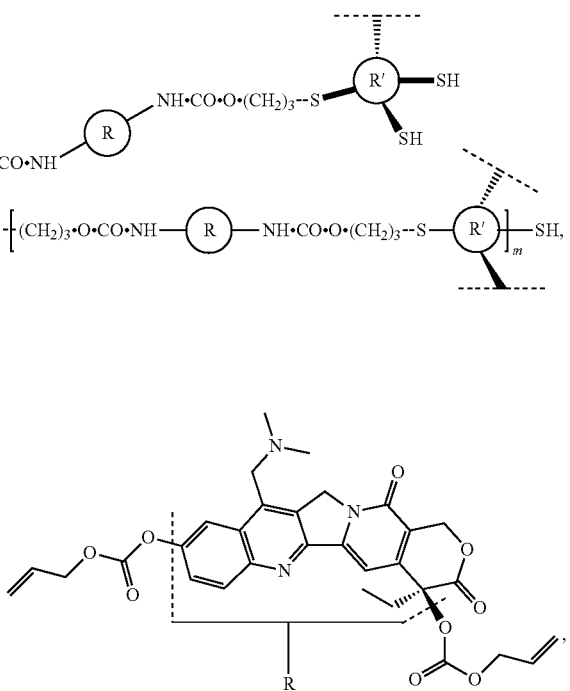

the monomer is selected from

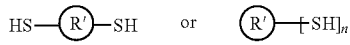

and the prepolymer is

wherein

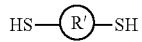

is selected from a group comprising dimercaptosuccinic acid, 2,3-dimercaptopropanol, 1,4-dithiothreitol, 1,4-butanedithiol, 2,3-dimercapto butane, 2-mercaptoehtyl ether, dithiol-PEG or dithiol containing substrates selected from oligosaccharides, peptides, oligonucleotides, and natural products; and
wherein

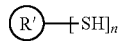

is selected from a group comprising pentaerythritol tetrakis (2-mercaptoacetate), pentaerythritol tetrakis (3-mercaptopropionate), Trimethylolpropane tris(2-mercaptoacetate), branched PEG thiol or synthetic oligothiol functionalized substrates selected from oligosaccharides, peptides, oligonucleotides, and natural products.

19. The biodegradable polymeric composition of claim 12, wherein said polymer is a ternary polymer having at least one active drug molecule and at least one said natural product.

* * * * *